United States Patent [19]
Beriger et al.

[11] 3,979,484
[45] Sept. 7, 1976

[54] O,S-DIALKYL-O-(1-METHOXYPHENYL-2-HALOVINYL)-DITHIOPHOSPHATES

[75] Inventors: Ernst Beriger; Jozef Drabek, both of Allschwil, Switzerland

[73] Assignee: Ciba-Geigy Corporation, Ardsley, N.Y.

[22] Filed: Feb. 26, 1975

[21] Appl. No.: 553,336

Related U.S. Application Data

[62] Division of Ser. No. 373,825, June 26, 1973, Pat. No. 3,879,499.

[30] Foreign Application Priority Data

June 27, 1972  Switzerland................... 9609/72
May 16, 1973  Switzerland................... 7060/73

[52] U.S. Cl................. 260/951; 424/217
[51] Int. Cl.²................ C07F 9/165; A01N 9/36
[58] Field of Search ................... 260/951

[56] References Cited
UNITED STATES PATENTS
3,116,201  12/1963  Whetstone et al............. 260/951 X

*Primary Examiner*—Anton H. Sutto
*Attorney, Agent, or Firm*—Frederick H. Rabin

[57] ABSTRACT

Compounds of the formula

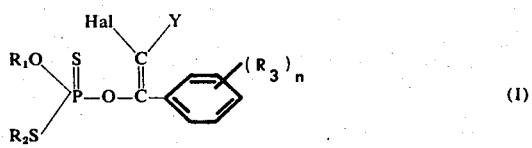

wherein
$R_1$ represents methyl or ethyl,
$R_2$ represents n-propyl, n-butyl, isobutyl or sec.butyl,
$(R_3)_n$ represents one or more hydrogen atoms, or represents similar or different chlorine, bromine, methyl or methoxy, $n$ is 1, 2 or 3, Y represents hydrogen or chlorine and Hal represents chlorine or bromine and their use of combating insects and members of the order Acarina are disclosed.

10 Claims, No Drawings

O,S-DIALKYL-O-(1-METHOXYPHENYL-2-HALOVINYL)-DITHIOPHOSPHATES

This is a division of application Ser. No. 373,825 filed on June 26, 1973, now U.S. Pat. No. 3,879,499.

The present invention relates to 0-1-phenyl-2-halovinylthio- and dithio-phosphoric acid esters, processes for their manufacture, and to their use in pest control. The compounds have the formula

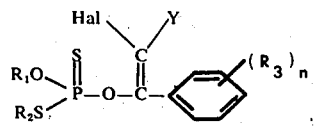

(I)

wherein $R_1$ represents methyl or ethyl,
$R_2$ represents n-propyl, n-butyl, isobutyl or sec.butyl,
$(R_3)_n$ represents one or more hydrogen atoms, or represents similar or different chlorine, bromine, methyl or methoxy, $n$ is 1,2, or 3, Y represents hydrogen or chlorine and Hal represents chlorine or bromine.

Preferred compounds on account of their action are those of the formula I, wherein $R_1$ represents methyl or ethyl, $R_2$ represents n-propyl, sec.butyl or isobutyl, $R_3$ represents hydrogen, chlorine, bromine, methyl or methoxy, $n$ is 1, 2 or 3, Y represents hydrogen or chlorine and Hal represents chlorine or bromine.

Particularly preferred compounds are those of the formula I, wherein $R_1$ represents ethyl, $R_2$ represents n-propyl, sec.butyl or isobutyl, $R_3$ represents hydrogen or chlorine, $n$ is 1, 2, or 3, Y represents hydrogen or chlorine and Hal represents chlorine.

The compounds of the formula I are manufactured by the following known methods:

1)

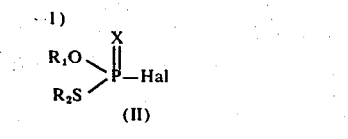

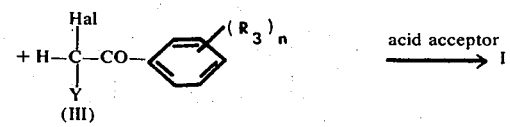 acid acceptor ⟶ I

2)

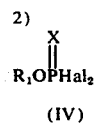

(IV)

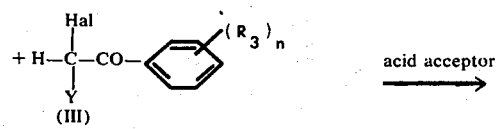 acid acceptor ⟶

 acid acceptor ⟶ I

 I

3)

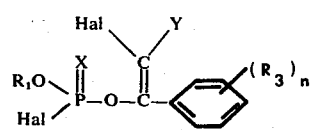

(VIII)

SOCl₂ or PCl₅ ⟶

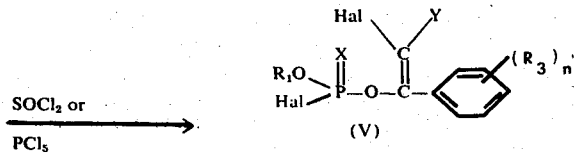

(V)

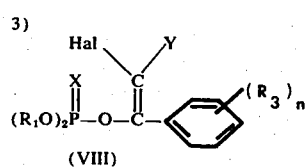

(V)

+ R₂SH (VI) acid acceptor ⟶ I

+ MeSR₂ (VII) ⟶ I

4) VIII + SOCl₂ or PCl₅ ⟶

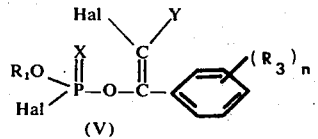

(IX)

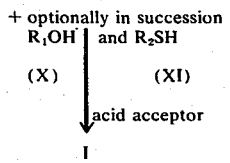

+ optionally in succession R₁OH and R₂SH
(X)    (XI)
acid acceptor
↓
I

5)

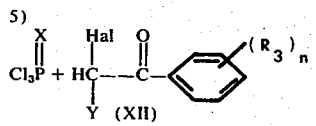

(XII)

acid acceptor ⟶

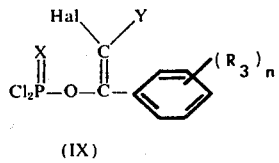

(IX)

+ optionally in succession

R₁OH (X) and R₂SH (XI)

↓ acid acceptor

I

In the formulae II to XII, $R_1$, $R_2$, $R_3$ X, Y, n, and Hal have the meanings given for the formula I and Me represents an alkali metal, in particular sodium or potassium, ammonium or $(C_1-C_4-alkyl)_3$ammonium.

Suitable acid acceptors are: tertiary amines, e.g. trialkylamines, pyridine, dialkyl anilines; inorganic bases, e.g. hydroxides; carbonates and bicarbonates of alkali metals and alkaline earth metals.

Processes 1 to 5 are carried out at a reaction temperature between −10° to 100°C, in particular between 20°–80°C, at normal or elevated pressure, and in solvents or diluents.

Examples of suitable solvents or diluents are: ether and ethereal compounds, e.g. diethyl ether, dipropyl ether dioxan, dimethoxy ethane, tetrahydrofuran; amides, e.g. N,N-dialkylated carboxylic acid amides; aliphatic, aromatic and halogenated hydrocarbons, in particular benzene, toluene, xylene, chloroform, chlorobenzene; nitriles, e.g. acetonitriles; sulphoxides, e.g. dimethyl-sulphoxide, ketones, e.g. acetone, methyl ethyl ketone.

Some of the starting materials of the formulae II, III, IV, VIII, IX, and XII are known or can be manufactured by methods and analogous to known ones.

The compounds of the formula I have a broad biocidal activity spectrum and can therefore be used for combating various plant and animal pests. In particular they are suitable for combating insects of the families: Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Tineidae, Noctuidae, Lymantriidae, Pyralidae, Galleriidae, Culicidae, Tipulidae, Stomoxydae, Muscidae, Calliphoridae, Trypetidae, Pulicidae, as well as Acaridae of the families: Ixodidae, Argasidae, Tetranychidae, Dermanyssidae.

By addition of other insecticides and/or acaricides, e.g. those listed in German Offenlegungschrift No. 2.248.307, pages 6 to 10, it is possible to improve substantially the insecticidal or acaricidal action and to adapt it to given circumstances.

Furthermore, the new compounds of the formula I act against plant parasitic nematodes.

The compounds of the formula I may be used as pure active substance or together with suitable carriers and/or additives. Suitable carriers and additives can be solid or liquid and correspond to the substances conventionally used in formulation technique such, for example, as solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology. Mention may also be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take, and be used in, the application forms described in German Offenlegungsschrift No. 2.248.307 on pages 12 to 18.

EXAMPLE 1

While stirred, 30.0 g O-ethyl-S-propylchlorodithiophosphate are added dropwise to a suspension of 6.25 g of NaOH (50 % oil suspension) in 150 ml of tetrahydrofuran. Then, while stirring, 30.7 g of 2-chloro-2',4'-dichloro-acetophenone are added dropwise over the course of 1½ hours at 25°–30°C. The reaction mixture is stirred for 3 hours at room temperature and for 1 hour at 40°–45°C. After carefully destroying the excess sodium hydride with 20 ml of absolute ethyl alcohol, the reaction mixture is diluted with 400 ml of water, the active substance extracted with benzene, and the benzene solution washed with water. The benzene is distilled off after the drying with $Na_2SO_4$, to yield the compound of the formula

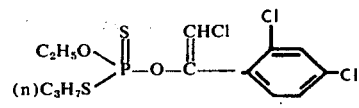

with a boiling point of 152°C/0,06 Torr in the form of a pale yellow oil.

The following compounds are also manufactured in analagous manner:

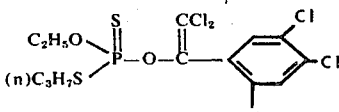   b.p.:140°C/0,001 Torr

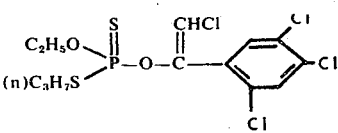   $n_D^{22}$ : 1,5767

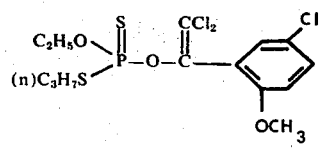 $n_D^{25}: 1.5130$

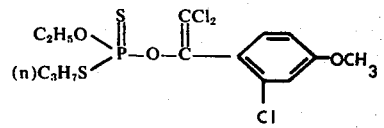 $n_D^{25}: 1.553$

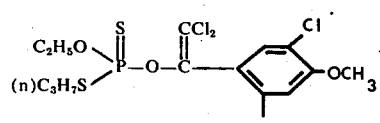 $n_D^{25}: 1.5162$

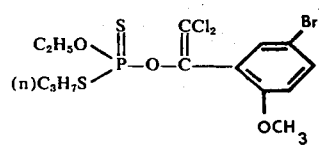 $n_D^{24}: 1.552$

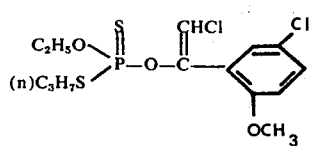 $n_D^{25}: 1.5545$

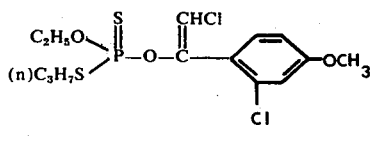 $n_D^{25}: 1.5588$

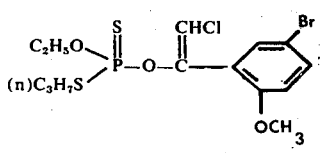 $n_D^{25}: 1.5668$

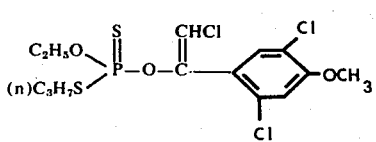 $n_D^{25}: 1.5718$

-continued

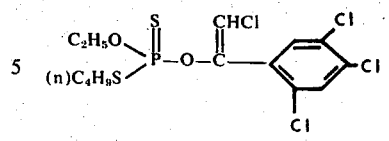 $n_D^{23}: 1.5642$

We claim:
1. A compound of the formula

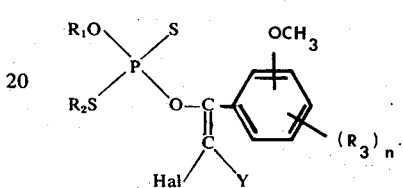

wherein $R_1$ is methyl or ethyl; $R_2$ is n-propyl, n-butyl, isobutyl or sec.butyl; each $R_3$ is hydrogen, chlorine or bromine; n is 1 or 2; y is hydrogen or chlorine; and Hal is chlorine or bromine.

2. A compound according to claim 1 in which $R_2$ is n-propyl, sec.butyl or isobutyl.

3. The compound of claim 2 which is O-ethyl-S-n-propyl-O-[1-(2-methoxy-5-chlorophenyl)-2,2-dichlorovinyl]-dithiophosphate.

4. The compound of claim 2 which is O-ethyl-S-n-propyl-O-[1-(2-chloro-4-methoxyphenyl)-2,2-dichlorovinyl]-dithiophosphate.

5. The compound of claim 2 which is O-ethyl-S-n-propyl-O-[1-(4-methoxy-2,5-dichlorophenyl)-2,2-dichlorovinyl]-dithiophosphate.

6. The compound of claim 2 which is O-ethyl-S-n-propyl-O-[1-(2-methoxy-5-bromophenyl)-2,2-dichlorovinyl]-dithiophosphate.

7. The compound of claim 2 which is O-ethyl-S-n-propyl-O-[1-(2-methoxy-5-chlorophenyl)-2-chlorovinyl]-dithiophosphate.

8. The compound of claim 2 which is O-ethyl-S-n-propyl-O-[1-(2-chloro-4-methoxyphenyl)-2-chlorovinyl]-dithiophosphate.

9. The compound of claim 2 which is O-ethyl-S-n-propyl-O-[1-(2-methoxy-5-bromophenyl)-2-chlorovinyl]-dithiophosphate.

10. The compound of claim 2 which is O-ethyl-S-n-propyl-O-[1-(4-methoxy-2,5-dichlorophenyl)-2-chlorovinyl]-dithiophosphate.

* * * * *